United States Patent [19]  [11] 4,414,017
Chan  [45] Nov. 8, 1983

[54] HERBICIDAL 3-BUTYROLACTONES

[75] Inventor: David C. K. Chan, Petaluma, Calif.

[73] Assignee: Chevron Research Company, San Francisco, Calif.

[21] Appl. No.: 153,476

[22] Filed: May 27, 1980

[51] Int. Cl.³ .................. A01N 43/08; A01N 43/10; C07D 333/32; C07D 307/32
[52] U.S. Cl. .......................... 71/88; 71/90; 71/98; 71/108; 71/116; 71/118; 549/65; 549/313; 560/21; 560/62
[58] Field of Search .................. 260/347.8, 343.6; 71/88, 90; 549/313, 65, 62

[56] References Cited
U.S. PATENT DOCUMENTS
4,227,914 10/1980 Fory et al. ...................... 71/88
4,284,566 8/1981 Bobner et al. ................ 260/343.6

FOREIGN PATENT DOCUMENTS
2724677 12/1978 Fed. Rep. of Germany .

Primary Examiner—Catherine L. Mills

[57] ABSTRACT
Compounds of the formula

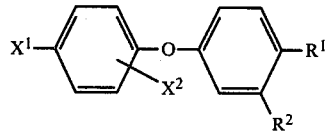

wheren $X^1$ is halo or trihalomethyl, $X^2$ is hydrogen or halo, $R^1$ is nitro or $-OR^3$, $R^2$ is hydrogen or $-OR^4$, $R^3$

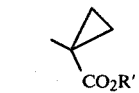

$R^4$ is

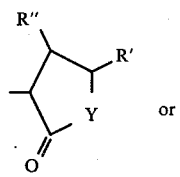

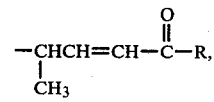

and R is hydroxy, alkoxy, alkenoxy, alkynoxy, thiol, alkythio, alkenylthio, amino, mono- or di-substituted amino or OM, wherein M is a monovalent cation; R' and R" are hydrogen, alkyl, alkenyl, alkynyl or phenyl; and Y is oxygen, sulfur, or substituted or unsubstituted nitrogen, have herbicidal activity.

13 Claims, No Drawings

HERBICIDAL 3-BUTYROLACTONES

BACKGROUND OF THE INVENTION

U.S. Pat. No. 4,163,661 discloses grass herbicides which are alkyl esters of 4-methyl-4-[4-(4'-trifluoromethylphenoxy)-phenoxy] crotonic acid.

U.S. Pat. No. 4,093,446 discloses herbicidal 4-trifluoromethyl-4'-nitrodiphenyl ethers.

U.S. Pat. No. 4,134,753 discloses herbicidal 4-halo-4'-nitro-3'-alkanoyloxy-diphenyl ethers.

SUMMARY OF THE INVENTION

This invention relates to novel herbicidal compounds, compositions and methods of use thereof. It has been found that certain phenoxy-phenoxy-carboxylic esters and lactones have herbicidal activity.

DESCRIPTION OF THE INVENTION

The compounds of the invention have the formula (I):

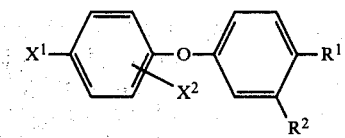

wherein $X^1$ is halo or trihalomethyl; $X^2$ is hydrogen or halo; $R^1$ is nitro or the group $-OR^3$; $R^2$ is hydrogen or the group $-OR^4$;

$R^3$ is

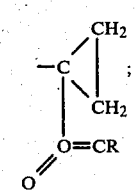

$R^4$ is

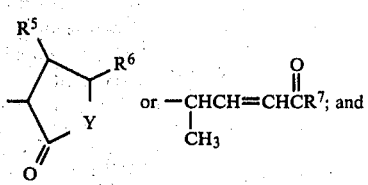

$R^5$ and $R^6$ are hydrogen, alkyl of 1 to 6 carbon atoms alkenyl of 2 to 6 carbon atoms, alkynyl of 2 to 6 carbon atoms or phenyl; with the proviso that when $R^1$ is nitro, $R^2$ is not hydrogen, and when $R^2$ is hydrogen, $R^1$ is not nitro;

$R^7$ is $-OM$, $-OR^8$, $-SR^8$, or $-NR^9R^{10}$, wherein $R^8$ is hydrogen, alkyl of 1 to 6 carbon atoms, alkenyl of 2 to 6 carbon atoms or alkynyl of 2 to 6 carbon atoms; $R^9$ and $R^{10}$ are individually hydrogen, alkyl of 1 to 6 carbon atoms, alkenyl of 2 to 6 carbon atoms, alkynyl of 2 to 6 carbon atoms, $-NR^{11}R^{12}$ or $-OR^{13}$, wherein $R^{11}$, $R^{12}$ and $R^{13}$ are individually defined as $R^8$ above and M is a monovalent inorganic cation or quaternary ammonium cation; and Y is oxygen, sulfur, or $-NR^{14}$ wherein $R^{14}$ is defined as $R^8$ above.

Representative $X^1$ groups are chloro, bromo, fluoro, iodo, trifluoromethyl, trichloromethyl. Preferably $X^1$ is trifluoromethyl.

Representative $X^2$ groups are chloro, bromo, fluoro, iodo and hydrogen. Preferably $X^2$ is in a position meta to $X^1$. Preferably $X^2$ is chloro.

Representative $R^3$ groups are 1-carboxy-cyclopropyl, 1-carbomethoxy-cyclopropyl, 1-carboethoxy-cyclopropyl, 1-carbobutoxy-cyclopropyl. Preferably, $R^3$ is 1-carbomethoxy-cyclopropyl.

Representative $R^4$ groups are 3-oxolan-2-one, 5-methyl-3-oxolan-2-one, 5-ethyl-3-oxolan-2-one, 5-butyl-3-oxolan-2-one, 3-thiolan-2-one, 5-phenyl-3-thiolan-2-one, 5-allyl-3-thiolan-2-one, 5-propargyl-3-thiolan-2-one, 3-azolidin-2-one, $-O-CH(CH_3)CH=CHCO_2H$, $-O-CH(CH_3)CH=CHCO_2CH_3$, $-O-CH(CH_3)CH=CHCO_2C_2H_5$, $-O-CH(CH_3)CH=CHCO_2C_3H_7$, $$-CH(CH_3)CH=CH\overset{O}{\overset{\|}{C}}ONa,$$

$$-CH(CH_3)CH=CH\overset{O}{\overset{\|}{C}}OCH_2CH=CH_2,$$

$$-CH(CH_3)CH=CH\overset{O}{\overset{\|}{C}}SC_2H_5, -CH(CH_3)CH=CH\overset{O}{\overset{\|}{C}}SH,$$

$$-CH(CH_3)CH=CH\overset{O}{\overset{\|}{C}}NHCH_3, -CH(CH_3)CH=CH\overset{O}{\overset{\|}{C}}NH_2,$$

$$-CH(CH_3)CH=CH\overset{O}{\overset{\|}{C}}NHCH_2CH=CH_2,$$

$$-CH(CH_3)CH=CH\overset{O}{\overset{\|}{C}}NHCH_2C\equiv CH,$$

$$-CH(CH_3)CH=CH\overset{O}{\overset{\|}{C}}NHNH_2,$$

$$-CH(CH_3)CH=CH\overset{O}{\overset{\|}{C}}NHN(CH_3)_2,$$

$$-CH(CH_3)CH=CH\overset{O}{\overset{\|}{C}}NHOH, -CH(CH_3)CH-CH\overset{O}{\overset{\|}{C}}NHOCH_3.$$

Preferably $R^4$ is 3-oxolan-2-one; 5-methyl-3-oxolan-2-one, and $-O-CH(CH_3)CH=CHCO_2CH_3$.

The compounds of the invention may be prepared according to the following scheme:

(1)
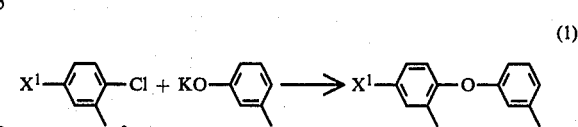

(2)
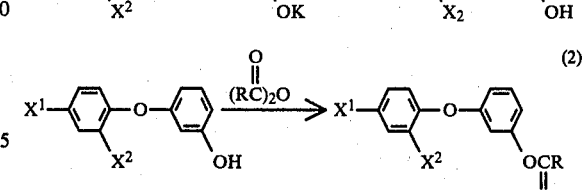

-continued

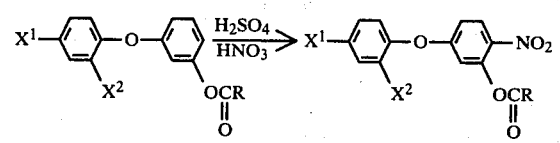
(3)

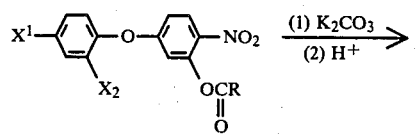
(4)

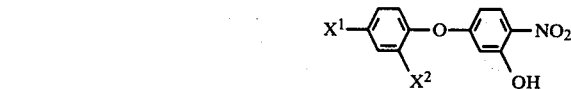

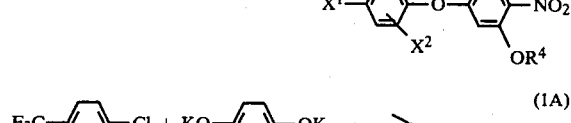
(5)

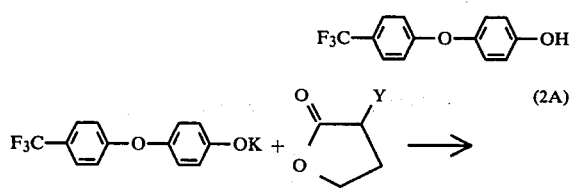

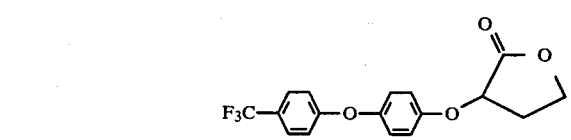
(1A)

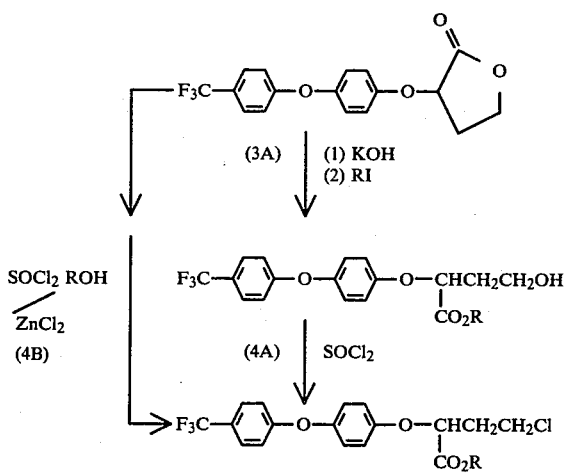

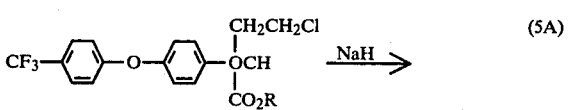

-continued

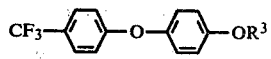

Steps (1) through (4) are known and may be carried out as described in U.S. Pat. No. 4,093,446, the entire disclosure of which is incorporated herein by reference, and as particularly described in Example 3, columns 16 and 17, therein.

Reaction (5) may be carried out at a temperature from 0° to 150° in an organic diluent. The phenoxide salt is prepared by treating the free phenol with a base, such as an alkali metal carbonate. Preferably, potassium carbonate is used. Other suitable bases include alkali metal hydroxides such as sodium hydroxide or potassium hydroxide, other carbonates such as sodium bicarbonate, alcoholates such as sodium ethylate and tertiary amines such as triethylamine, dimethyl aniline, pyridine, etc. Reaction (5) is shown above as being conducted with a hydrocarbyl bromide, $R^4Br$, as a reactant, however, an analogous chloride, fluoride or iodide may also be used.

Step (1A) is analogous to step (1) and step (2A) is analogous to step (5). Step (3A) is a conventional lactone-ring opening, followed by conventional esterification. Step (4A) may be conducted in a suitable organic diluent, from 0° to 100° C., preferably between 15° and 40° C. A mixture of products is obtained of which about 25% is the desired gamma-chloro ester.

The preferred route to the gamma-chloro ester is step (4B), which may be conducted in the appropriate alcohol at its reflux temperature, to obtain the desired ester. A slight molar excess of thionyl chloride is used with a catalytic amount of zinc chloride.

Step (5A) may be conducted in an organic diluent at 0° to 100° C., preferably at ambient temperature, using a molar equivalent of sodium hydride. It is necessary that solvents not containing an active hydrogen be used, such as ethers and glycol ethers, such as 1,2-dimethoxyethane.

UTILITY

The compounds of the present invention are, in general, herbicidal in both pre- and post-emergency applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are particularly effective against broadleaved weeds. Some may be selective with respect to the type of application and/or type of weed.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees. The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of active compound or composition administered will vary with the particular plant part or plant growth medium which is to be contacted, the general location of application—i.e., sheltered areas such as greenhouses, as compared to exposed areas such as fields—as well as the desired type of control. Generally for both pre- and post-emergent herbicidal control, the compounds of the invention are applied at rates of 0.2 to 60 kg/ha, and the preferred rate is in the range of 0.5 to 40 kg/ha. For plant growth regulating or retarding activity, it is essential to apply the compounds at a concentration not so high as to kill the plants. Therefore, the application rates for plant growth regulating or retarding activity will generally be lower than the rates used for killing plants. Generally, such rates vary from 0.1 to 5 kg/ha, and preferably from 0.1 to 3 kg/ha.

Herbicidal tests on representative compounds of the invention were made using the following methods.

Pre-Emergent Herbicidal Test

An acetone solution of the test compound was prepared by mixing 375 mg. of the compound, 118 mg. of a nonionic surfactant and 18 ml. of acetone. 10 ml. of this solution was added to 40 ml. of water to give the test solution.

Seeds of the test vegetation were planted in a pot of soil and the test solution was sprayed uniformly onto the soil surface at a dose of $27.5\mu/cm^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, representing no phytotoxicity, 100 representing complete kill. The results of these tests appear in Table II.

Post-Emergent Herbicidal Test

The test compound was formulated in the same manner as described above the pre-emergent test. This formulation was uniformly sprayed on 2 similar pots of 24-day-old plants (approximately 15 to 25 plants per pot) at a dose of $27.5\mu/cm^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

EXAMPLE 1

Preparation of 3-[5-(2'-chloro-4'-trifluoromethyl phenoxy)-2-nitro-phenoxy]-butyrolactone A mixture of 4.6 g. of 5-(2'-chloro-4'-trifluoromethylphenoxy)-2-nitrophenol (U.S. Pat. No. 4,093,446), 3-bromobutyrolactone (Aldrich, 3.0 g.) and potassium carbonate (5.0 g.) in 50 ml. 2-butanone was stirred and refluxed for 18 hours.

The solvent was stripped (reduced pressure) and the residue was diluted with 150 ml. water, extracted with diethyl ether ($2\times75$ ml.). The ether phase was collected, washed (water), dried ($MgSO_4$), filtered and stripped to 5.2 g. which was purified on a 200 g. silica gel column. The title compound was eluted with 5% acetone: 25% diethyl ether:pet. ether; 3.2 g., m.p. 101°–106° C.

EXAMPLE 2

Preparation of Methyl 4-[5-(2'-chloro-4'-trifluoromethylphenoxy)-2-nitro-phenoxy]-4-methyl-crotonate A mixture of 5-(2'-chloro-4'-trifluoromethyl phenoxy)-nitrophenol (16 g.), methyl 4-bromo-4-methyl crotonate (12 g.) and potassium carbonate (11 g.) in 250 mls. 2-butanone was stirred and refluxed for 18 hours.

Work-up and purification was similar to Example 1 to yield 9.1 g. of the title product (oil).

EXAMPLE 3

Preparation of 1-[4-(4'-trifluoromethylphenoxy)-phenoxy]-1-carbomethoxy-cyclopropane A. 3-[4-(4'-trifluoromethylphenoxy)-phenoxy]-butyrolactone (10.7 g.) in 100 ml. methanol was treated with a solution of 2.0 g. potassium hydroxide (90%) in 10 ml. water. After stirring at ambient temperature overnight, the solvent was stripped to yield an oily residue which in turn was dissolved in 100 ml. methyl ethyl ketone. Iodomethane (6 g.) was added to the solution and the mixture was stirred overnight.

The solvent was stripped, 200 ml. dichloromethane was added and the mixture was washed with water (100 ml.). The aqueous extract was backwashed with dichloromethane (100 ml.). The combined dichloromethane solutions were washed with water, dried (MgSO$_4$) and filtered. The solvent was stripped to yield a crude oil (10.1 g.) containing methyl 2-[4-(4'-trifluoromethylphenoxy)-phenoxy]-4-hydroxy-butanoate.

B. The oil isolated above was dissolved in 150 ml. dichloromethane and 1 ml. DMF. To this solution 6.0 g. of thionyl chloride was added rapidly and stirring was continued at room temperature overnight. The solvent was stripped and methylene chloride (150 ml.) was added. Pyridine (2.8 g.) in methanol (2.0 g.) was added dropwise, then the mixture was stirred for 1½ hrs. at room temperature and for 1 hr. at reflux. The solution was stripped, and the residue was dissolved in dichloromethane (150 ml.), washed (water: 100 ml.; 10% HCl: 50 ml.; water: 50 ml.), dried (MgSO$_4$), and filtered. The filtrate was stripped to yield an oil which was purified on silica gel (200 g.) by election with varying ratios of diethyl ether/pet. ether. The fractions containing methyl 2-[4-(4'-trifluoromethylphenoxy)-phenoxy]-4-chloro-butanoate were combined and stripped to yield 3.4 g. oil.

C. The gamma-chloro ester from 3B above was dissolved in 50 ml. 1,2-dimethoxyethane and 0.52 g. sodium hydride was rapidly added. The slurry was stirred at room temperature for two days. The solvent was stripped and the residue was slurried in dichloromethane. A few drops of methanol and then 25 ml. of water were added. The organic layer was collected, dried (MgSO$_4$), filtered and stripped to yield an oil which crystallized. Trituration with pet. ether at 0° C. yielded 1.6 g. of the title product (solid). The filtrate from crystallization was stripped and crystallized (diethyl ether) to yield an additional 0.7 of the title product, m.p. 82°–84° C.

EXAMPLE 4

Preparation of 1-[4-(4'-trifluoromethylphenoxy)-phenoxy]-1-carbomethoxy-cyclopropane A. 3-[4-(4'-trifluoromethylphenoxy)-phenoxy]-butyrolactone, 0.057 mol, prepared by methods analogous to Example 1, and a catalytic amount of zinc chloride are stirred in 150 ml. anhydrous methanol while 0.067 mol. thionyl chloride is added. The mixture is stirred at room temperature for one hour and refluxed mildly for 3 hours. The solvent is stripped under reduced pressure and the residue is purified on a silica gel (200 g.) column. Methyl 2-[4-(4'-trifluoromethylphenoxy)-phenoxy]-4-chlorobutanoate is eluted with 5% diethyl ether/pet. ether.

B. Methyl 2-[4-(4'-trifluoromethylphenoxy)-phenoxy]-4-chloro-butanoate is treated with sodium hydride under conditions described in Example 3C to yield the title product.

EXAMPLE 5

Preparation of 3-methyl-3-[3-(2'-chloro-4'-trifluoromethylphenoxy)-phenoxy]-butyrolactone 3-[3-(2'-chloro-4'-trifluoromethylphenoxy)-phenoxy]-butyrolactone (5.0 g.) was prepared by a method analogous to Example 1 above and dissolved in 25 ml. tetrahydrofuran (THF). To a second solution of hexamethyl disilane (2.2 g., 98%) in 10 ml. THF under nitrogen atmosphere at 0° C. was added dropwise 8.4 ml. of a 1.6 M solution of n-butyl lithium in hexane. The first solution (butyrolactone) was added dropwise to the second solution over a period of 1¼ hrs., then stirred in a dry-ice acetone bath for 30 minutes. Then 2.0 g. of iodomethane was added rapidly and the solution was allowed to reach room temperature and was stirred overnight. The dark-brown solution was stripped and the residue was dissolved in 125 ml. dichloromethane, washed with dilute acid (50 ml.), water (50 ml.) and brine (50 ml.), dried (MgSO$_4$), filtered and stripped. The resultant amber oil (5.3 g.) was dissolved in diethyl ether and chromatographed on a silica gel (200 g.) column. The column was eluted with diethyl ether/pet. ether and the fractions containing the title product were combined and stripped to yield an oil (300 mg.).

TABLE I

COMPOUNDS OF THE FORMULA

F$_3$C—⟨phenyl(X$^2$)⟩—O—⟨phenyl(R$^2$)⟩—R$^1$

| No. | R$^1$ | R$^2$ | X$^2$ | mp °C. | C CAL. | C Fd. | H CAL. | H Fd. | N CAL. | N Fd. |
|---|---|---|---|---|---|---|---|---|---|---|
| 1 | | | | | | | | | | |
| 1 | NO$_2$ | 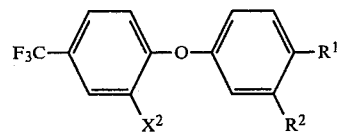 | Cl | 101–106 | 48.88 | 49.0 | 2.65 | 2.44 | 3.35 | 3.38 |

TABLE I-continued

COMPOUNDS OF THE FORMULA

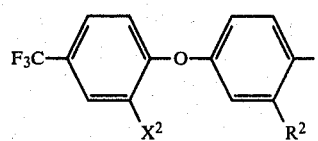

| No. | R¹ | R² | X² | mp °C. | C CAL. | C Fd. | H CAL. | H Fd. | N CAL. | N Fd. |
|---|---|---|---|---|---|---|---|---|---|---|
| 2 | NO₂ | OCHCH=CHCO₂CH₃ \| CH₃ | Cl | Oil | 51.19 | 51.19 | 3.39 | 2.96 | 3.14 | 3.59 |
| 3 | NO₂ | (CH₃-substituted lactone) | Cl | Oil | 50.19 | 47.75 | 2.81 | 3.04 | 3.75 | 3.19 |
| 4 | (cyclopropyl CO₂CH₃ ether) | H | H | 82–84 | 61.36 | 61.01 | 4.29 | 4.28 | — | — |
| 5 | H | (CH₃-substituted lactone) | Cl | Oil | 55.9 | 54.81 | 3.65 | 4.02 | 0 | 0.16 |

TABLE II

HERBICIDAL ACTIVITY

| | Pre/Post | % Control | | | | |
|---|---|---|---|---|---|---|
| No | L | M | P | C | W | O |
| 1 | 70/98 | 100/100 | 100/100 | 88/90 | 43/95 | 15/73 |
| 2 | 100/100 | 100/100 | 100/100 | 100/70 | 75/100 | 45/95 |
| 3 | 100/100 | 100/100 | 100/100 | 100/63 | 98/100 | 35/70 |
| 4 | 0/22 | 0/12 | 0/10 | 100/75 | 100/90 | 35/25 |

L = Lambsquarter (*Chenopodium album*)
M = Mustard (*Brassica arvensis*)
P = Pigweed (*Amaranthus retroflexus*)
C = Crabgrass (*Digitaria Sanguinalis*)
W = Watergrass (*Echinochloa crusgalli*)
O = Wild Oats (*Avenua fatua*)

What is claimed is:

1. A compound having the formula:

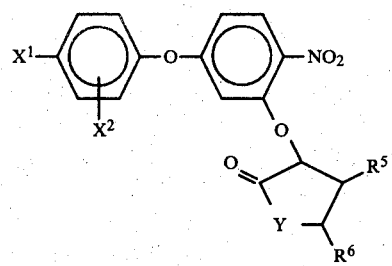

wherein
$X^1$ is halo or trihalomethyl;
$X^2$ is hydrogen or halo; Y is oxygen or sulfur and
$R^5$ and $R^6$ are independently hydrogen, alkyl of 1 to 6 carbon atoms, alkenyl of 2 to 6 carbon atoms, alkynyl of 2 to 6 carbon atoms or phenyl.

2. A compound having the formula:

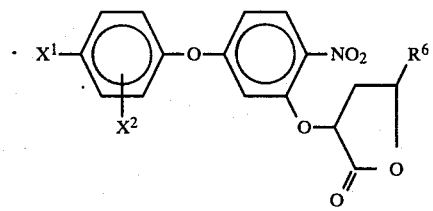

wherein
$X^1$ is halo or trihalomethyl;
$X^2$ is hydrogen or halo and
$R^6$ is hydrogen, alkyl of 1 to 6 carbon atoms, alkenyl of 2 to 6 carbon atoms or phenyl.

3. The compound of claim 2 wherein $X^1$ is trihalomethyl and $X^2$ is meta-chloro with respect to $X^1$.

4. A compound according to claim 1 wherein $X^1$ is trihalomethyl.

5. A compound according to claim 1 wherein $R^1$ is nitro and $X^2$ is meta-chloro with respect to $X^1$.

6. The compound according to claim 3 wherein $R^6$ is hydrogen and $X^1$ is trifluoromethyl.

7. The compound according to claim 3 wherein $R^6$ is methyl and $X^1$ is trifluoromethyl.

8. A method for the control of undesirable vegetation which comprises applying to said vegetation or its habitat an herbicidally effective amount of a compound of the formula defined in claim 1.

9. An herbicidal composition comprising a biologically inert carrier and an herbicidally effective amount of a compound of the formula defined in claim 1.

10. A method for the control of undesirable vegetation which comprises applying to said vegetation or its habitat an herbicidally effective amount of a compound of the formula defined in claim 2.

11. An herbicidal composition comprising a biologically inert carrier and an herbicidally effective amount of a compound of the formula defined in claim 2.

12. A method for the control of undesirable vegetation which comprises applying to said vegetation or its habitat an herbicidally effective amount of a compound of the formula defined in claim 3.

13. An herbicidal composition comprising a biologically inert carrier and an herbicidally effective amount of a compound of the formula defined in claim 3.

* * * * *

UNITED STATES PATENT AND TRADEMARK OFFICE
CERTIFICATE OF CORRECTION

PATENT NO. : 4,414,017
DATED : November 8, 1983
INVENTOR(S) : David C. K. Chan

It is certified that error appears in the above—identified patent and that said Letters Patent are hereby corrected as shown below:

Col. 1, line 40, formula "$\underset{O}{\overset{}{\diagup}}O\!=\!CR$" should read $--\underset{O}{\overset{}{\diagup\!\!\!\!\diagup}}CR^7--$ Signed and Sealed this Seventh Day of February 1984

[SEAL]

Attest:

GERALD J. MOSSINGHOFF

Attesting Officer

Commissioner of Patents and Trademarks